United States Patent [19]

Venturello et al.

[11] Patent Number: 4,866,178
[45] Date of Patent: Sep. 12, 1989

[54] PROCESS FOR THE PREPARATION OF 2-CARBOXYPYRAZINE 4-OXIDES

[75] Inventors: Carlo Venturello; Rino D'Aloisio, both of Novara, Italy

[73] Assignee: Montedison S.p.A., Milan, Italy

[21] Appl. No.: 152,471

[22] Filed: Feb. 5, 1988

Related U.S. Application Data

[63] Continuation-in-part of Ser. No. 863,425, May 15, 1986, abandoned.

[30] Foreign Application Priority Data

May 17, 1985 [IT] Italy ................................. 20780 A/85

[51] Int. Cl.⁴ .......................................... C07D 241/18
[52] U.S. Cl. .................................................. 544/406
[58] Field of Search .......................................... 544/406

[56] References Cited

U.S. PATENT DOCUMENTS 3,702,831 11/1972 Chiavellier et al. ................. 546/246
4,002,750 1/1977 Ambrogi et al. .................... 544/406

FOREIGN PATENT DOCUMENTS 0201934 11/1986 European Pat. Off. .

OTHER PUBLICATIONS

Kobayashi et al., Chem. Pharm. Bull. 22(9), 2097–2100, (1974).

Nagy, et al., Chem. Abstracts, vol. 100 (1984), entry 51464v.

*Primary Examiner*—Cecilia Shen
*Attorney, Agent, or Firm*—Stevens, Davis, Miller & Mosher

[57] ABSTRACT

A process for the preparation of 2-carboxypyrazine 4-oxides having the formula (I)

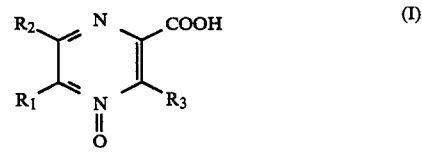

wherein $R_1$, $R_2$ and $R_3$, which may be the same or different, represent a hydrogen atom or an alkyl group having from 1 to 6 carbon atoms, by oxidation of the corresponding 2-carboxypyrazines. The 2-carboxypyrazines are reacted under stirring with an aqueous solution of $H_2O_2$, at a pH ranging between 0.5 and 5, in the presence of a catalyst selected from the group consisting of tungstic acid, a isopolytungstic acid, a heteropolytungstic acid, molybdic acid, an isopolymolybidic acid, a heteropolymolybdic acid, and an alkali metal salt thereof.

13 Claims, No Drawings

PROCESS FOR THE PREPARATION OF 2-CARBOXYPYRAZINE 4-OXIDES

CROSS REFERENCE TO RELATED APPLICATION

This application is a continuation-in-part of Ser. No. 863,425, filed May 15, 1986 abandoned.

DESCRIPTION OF THE INVENTION

The present invention relates to a process for the preparation of 2-carboxypyrazine 4-oxides having the formula (I):

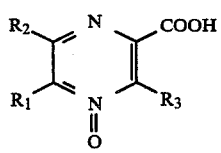

wherein $R_1$, $R_2$ and $R_3$, which may be the same or different, represent a hydrogen atom or an alkyl group having from 1 to 6 carbon atoms.

More precisely, the present invention relates to a process for the preparation of the aforesaid 2-carboxypyrazine 4-oxides (I), by catalytic oxidation by means of $H_2O_2$, of the corresponding 2-carboxypyrazines having the formula (II):

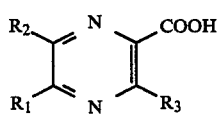

2-carboxypyrazine 4-oxides (I), wherein at least one of $R_1$, $R_2$ and $R_3$ groups is an alkyl radical, are pharmaceutical products having hypoglycaemic and hypolipaemic activity.

It is known that the N-oxidation of heterocyclic bases, including the diazinic derivatives, is generally carried out by using, as oxidizing agents, organic per-acids, produced separately or prepared in situ, starting from $H_2O_2$ and the corresponding acids, for instance acetic acid, formic acid and maleic acid.

It is also known that the N-oxidation of 2-carboxypyrazines by means of the aforesaid oxidizing agents in some cases cannot occur, whereas in other cases it does not give good yields and/or it is not regioselective. In the case of non-substituted 2-carboxypyrazine, i.e., compound (I) wherein $R_1$, $R_2$ and $R_3$ are hydrogen atoms, it is impossible to obtain any N-oxide by means of organic per-acids. In the case of substituted 2-carboxypyrazines (for instance 2-carboxy-5-methylpyrazine), using either per-formic or per-acetic acid, the corresponding 4-oxide is obtained in admixture with 1-oxide and 1,4-dioxide, thus giving rise to difficult and expensive separation problems, whereas by using per-maleic acid, and by working at 0° C., the 4-oxide can be obtained, but only with unsatisfactory yields and after a particularly long reaction time of about 2 days.

Therefore the direct oxidation of 2-carboxypyrazines to 2-carboxypyrazine 4-oxides by means of organic per-acids cannot be industrially exploited.

On the contrary, the 2-carboxypyrazine 4-oxides having formula (I) can be obtained in a selective way starting from the corresponding 2-carboxypyrazine having the formula (II) by a several-stage process, that involves the conversion of the 2-carboxypyrazine (II) into the corresponding amide (III) through the intermediate formation of a mixed anhydride, according to the reaction scheme indicated hereinafter. Following this comes the regioselective N-oxidation of the amide (III) to the 4-oxide (IV) by means of per-acetic acid, and the subsequent conversion of the 4-oxide (IV) into the desired compound (I) by saponification such as by means of NaOH.

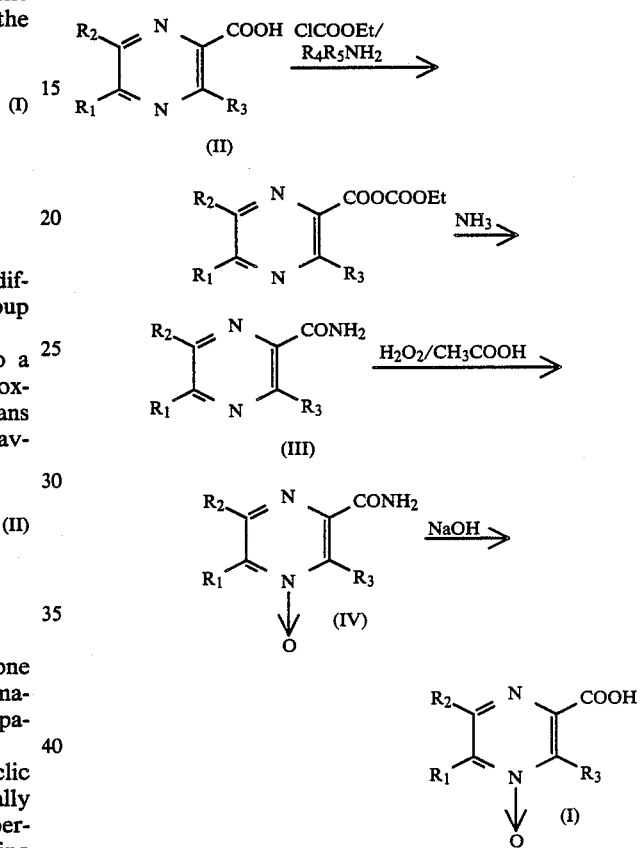

This polystage process is long, toilsome and burdensome from an economic point of view.

Furthermore the N-oxidation stage requires a large excess of organic acid to form in situ the per-acid, which must be present at least in stoichiometric amounts in comparison with the substratum to be oxidized. Finally the separation of the organic acid at the end of the reaction requires peculiar or delicate operations.

It is an object of the present invention to provide a simple and economic process in order to obtain, in only one stage 2-carboxypyrazine 4-oxides having formula (I) by catalytic oxidation, by means of $H_2O_2$, of 2-carboxypyrazines having formula (II).

It is another object of the invention to provide a process which allows one to obtain 2-carboxypyrazine 4-oxides (I) with a good yield and in a selective way.

It is another object of the invention to avoid using organic per-acids, thereby avoiding the drawbacks connected with the use of great quantities of organic acids which are precursors of the per-acids and consequently without the need for separation of such acids at the end of the reaction.

These and still other objects are attained by the process, according to the present invention, for the preparation of 2-carboxypyrazine 4-oxides having formula (I) by oxidation of the corresponding 2-carboxypyrazines having the formula (II). This process is characterized in that 2-carboxypyrazines (II) are reacted under stirring with an aqueous solution of $H_2O_2$ at a pH ranging between 0.5 and 5, in the presence of a catalyst selected from the group consisting of tungstic acid, an isopolytungstic acid, a heteropolytungstic acid molybdic acid, an isopolymolybdic acid, a heteropolymolybdic acid, and an alkali metal salt thereof.

In fact we have found, according to the present invention, that whereas the direct N-oxidation of 2-carboxypyrazines (II) by means of organic per-acids does not occur in some cases and gives low yields and/or is not selective with respect to the desired 4-oxide in other cases, the same reaction occurs with formation of the 4-oxide with good yields and in a selective way, when use is made of a catalyst of the present invention.

The reaction is generally carried out at temperatures ranging between 0° and 100° C. Preferably the reaction is carried out at temperatures between about 60° C. and about 90° C. Usually one works at substantially atmospheric pressure.

As the starting 2-carboxypyrazines (II), one prefers to employ those wherein one of the $R_1$, $R_2$ or $R_3$ substituent groups is an alkyl group having from one to six carbon atoms, whereas the two remaining substituents are hydrogen atoms. The methyl group is the preferred alkyl group. 2-carboxy-5-methylpyrazine is one of the most preferred starting compounds.

As explained hereinbefore, the catalyst is selected from the group consisting of tungstic acid, an isopolytungstic acid, a heteropolytungstic acid, molybdic acid, an isopolymolybdic acid, a heteropolymolybdic acid, and the alkali metal salts (in particular the sodium and potassium salts) of these acids.

Among the heteropolytungstic acids, use may be made for instance of phosphotungstic acid, arsenotungstic acid, and borotungstic acid.

Among the heteropolymolybdic acids, use may be made for instance of phosphomolybdic acid and arsenomolybdic acid.

The tungsten compounds are preferred as they are endowed with a higher catalytic activity. Tungstic acid and its alkali metal salts are chiefly preferred.

The catalyst can be formed "in situ" in the reaction medium as well, by introducing into the reactor, together with $H_2O_2$, water, and optionally 2-carboxypyrazine (I), a tungsten or molybdenum compound, capable of turning into the tungstate or the molybdate ion in the reaction medium, and by then bringing the pH to a value ranging between 0.5 to 5. Tungsten and molybdenum compounds, suitable for converting into the tungstate or the molybdate ion in the reaction medium, are for instance $WO_2$, $W_2O_5$, $WO_3$, $WS_2$, $WS_3$, $WCl_6$, $WOCl_4$, $W(CO)_6$, $Mo_2O_3$, $Mo_2O_5$, and $MoO_3$.

As explained hereinbefore, the reaction is carried out at a pH ranging between 0.5 and 5. Preferably one works at a pH between about 1.0 and 2.0.

The catalyst is generally used in amounts ranging between 0.01 and 1 mole of W or Mo per mole of substratum, and preferably between 0.01 and 0.05 moles of W or Mo per mole of substratum.

2-carboxypyrazine (II) and $H_2O_2$ may be used in a 1:1 molar ratio, corresponding to the reaction stoichiometry. Preferably, use is made of a slight excess of $H_2O_2$ (for instant 10–30%) compared with the stoichiometric amount.

The starting concentration of $H_2O_2$ in the aqueous solution of $H_2O_2$ generally ranges between 1 and 20% by weight, and preferably between about 5% and about 10%.

The reaction is carried out, for instance, as follows: an aqueous solution is prepared containing $H_2O_2$ and the selected catalyst and this solution is brought to the desired pH by means of dilute mineral acids or bases (for instance HCl, $H_2SO_4$ or NaOH). The substratum is added to the aqueous solution and the whole is treated, under fairly strong stirring, at the desired temperature until completion of the reaction is reached. The desired product, sometimes, may already start to precipitate by the end of the reaction, and when the reaction is over, it cold-precipitates, at least for the most part.

The invention is still further illustrated by the following examples.

EXAMPLE 1

330 mg (1 mmole) of $Na_2WO_4.2H_2O$ were dissolved in 16 ml of $H_2O$ in a 50 ml flask, equipped with mechanical stirrer, reflux cooler, and thermometer. 3.75 ml of $H_2O_2$ at 40% weight/volume (400 g/l) (44 mmoles) were added to the solution and the pH of same was brought to 1.5 by means of dilute $H_2SO_4$. The 5.52 g (40 mmoles) of 2-carboxy-5-methylpyrazine were introduced.

The resulting aqueous suspension was heated under stirring to 70° C. for 2½ hours thereby obtaining a gradual solubilization of the suspension. Near the end, a partial precipitation of the reaction product from the solution was noted. At the end, the mixture was left to settle at room temperature overnight, thereby obtaining a substantial precipitation of the product in the crystalline form.

The product was filtered, washed with a little icy water, and dried on a porous plate.

4.68 g of 2-carboxy-5-methylpyrazine 4-oxide were obtained, partly in the hydrated form (2.83% of water), equal to 4.54 g of anhydrous product. The yield was 73%.

EXAMPLE 2

250 mg (0.75 mmoles) of $Na_2WO_4.2H_2O$ were dissolved in 13 ml of $H_2O$ in a 50 ml flask, equipped with mechanical stirrer, reflux cooler, and thermometer. 3.23 ml of $H_2O_3$ at 40% weight/volume (38 mmoles) were added to the solution and the pH of same was brought to 2.0 by means of dilute $H_2SO_4$. Then 3.76 g of 2-carboxypyrazine at 98% (30 mmoles) were introduced.

The resulting aqueous suspension was heated under stirring to 80° C. for 2 hours, thereby obtaining a complete solubilization of the suspension after 45 minutes. At the end, the solution was left to settle overnight at room temperature, thereby obtaining the precipitation of the reaction product in the crystalline form. The product was filtered, washed with a little icy water, and dried on a porous plate.

3.02 g of 2-carboxypyrazine 4-oxide monohydrate were obtained (found $H_2O=11.35\%$; calculated water for the monohydrate product: 11.39%). The yield was 63%.

What is claimed is:

1. A process for the manufacture of a 2-carboxypyrazine 4-oxide having the formula (I):

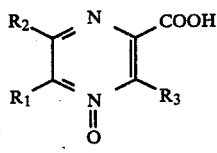

(I)

wherein $R_1$, $R_2$ and $R_3$ are the same or different, and represent a hydrogen atom or an alkyl group having from 1 to 6 carbon atoms, by oxidation of the corresponding 2-carboxypyrazine having the formula (II):

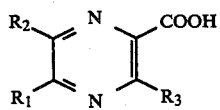

(II)

characterized in that a carboxypyrazine (II) is reacted under stirring with an aqueous solution of $H_2O_2$ at a pH between 0.5 and 5, in the presence of a catalyst selected from the group consisting of tungstic acid, an isopolytungstic acid, arsenotungstic acid, borotungstic acid, molybdic acid, an isopolymolybdic acid, phosphomolybdic and arsenomolybdic acid, and alkali metal salts thereof.

2. The process according to claim 1, wherein the temperature is between 0° and 100° C.

3. The process according to claim 2, wherein the temperature is substantially between 60° C. and 90° C.

4. The process according to claim 1, wherein one of $R_1$, $R_2$ and $R_3$ is an alkyl group having from 1 to 6 carbon atoms, and the two remaining are hydrogen atoms.

5. The process according to claim 4, wherein the alkyl group having from 1 to 6 carbon atoms is a methyl group.

6. The process according to claim 1, wherein the catalyst is selected from the group consisting of tungstic acid, isopolytungstic acid, arsenotungstic acid, borotungstic acid, and alkali metal salts thereof.

7. The process according to claim 6, wherein the catalyst is tungstic acid or an alkali metal salt thereof.

8. The process according to claim 1, wherein the pH is substantially between 1.0 and 2.0.

9. The process according to claim 1, wherein the molar ratio between the catalyst, calculated as W or Mo, and the carboxypyrazine (II) ranges between 0.01 and 1.

10. The process according to claim 9, wherein said molar ratio ranges between 0.01 and 0.05.

11. The process according to claim 1, wherein the molar ratio between the $H_2O_2$ and the 2-carboxypyrazine (II) ranges between 1.0 and 1.3.

12. The process according to claim 1, wherein the $H_2O_2$ starting concentration in the aqueous solution ranges between 1 and 20% by weight.

13. The process according to claim 12, wherein said $H_2O_2$ substantially ranges between 5% and 10% by weight.

* * * * *